US011801037B2

(12) United States Patent
Miyachi (10) Patent No.: US 11,801,037 B2
(45) Date of Patent: Oct. 31, 2023

(54) ULTRASOUND SYSTEM AND METHOD FOR CONTROLLING ULTRASOUND SYSTEM

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/060,206

(22) Filed: Oct. 1, 2020

(65) Prior Publication Data

US 2021/0015462 A1    Jan. 21, 2021

Related U.S. Application Data

(63) Continuation of application No. PCT/JP2019/016625, filed on Apr. 18, 2019.

(30) Foreign Application Priority Data

Apr. 25, 2018    (JP) .................................. 2018-084305

(51) Int. Cl.
*A61B 8/00*    (2006.01)
*A61B 8/14*    (2006.01)
*A61B 8/08*    (2006.01)

(52) U.S. Cl.
CPC ................ *A61B 8/461* (2013.01); *A61B 8/14* (2013.01); *A61B 8/4444* (2013.01); *A61B 8/4494* (2013.01); *A61B 8/5215* (2013.01)

(58) Field of Classification Search
CPC ......... A61B 8/461; A61B 8/14; A61B 8/4444; A61B 8/4494; A61B 8/5215; G06T 2207/10132; G06T 2207/20132
See application file for complete search history.

(56) References Cited

U.S. PATENT DOCUMENTS

| 5,538,004 A | 7/1996 | Bamber |
| 5,640,959 A | 6/1997 | Hara et al. |

(Continued)

FOREIGN PATENT DOCUMENTS

| JP | H07-231892 A | 9/1995 |
| JP | 2002-224101 A | 8/2002 |

(Continued)

OTHER PUBLICATIONS

International Search Report issued in PCT/JP2019/016625; dated Jul. 16, 2019.

(Continued)

*Primary Examiner* — Colin T. Sakamoto
*Assistant Examiner* — Tommy T Ly
(74) *Attorney, Agent, or Firm* — Studebaker & Brackett PC (57) ABSTRACT

An ultrasound system 1 includes an ultrasound probe 2 and an image display device 3. The ultrasound probe 2 includes a transducer array 11 including a plurality of transducers, a transmitting and receiving unit 14 that transmits and receives ultrasonic waves using an aperture transducer group consisting of some transducers to generate a sound ray signal, and an image information data generation unit 19 that generates image information data from the sound ray signal. The image display device 3 includes a display unit 34. One of the ultrasound probe 2 and the image display device 3 includes a display image region determination unit 22 that determines a display image region obtained by excluding a shallow image region from an ultrasound image on the basis of the width of all of the transducers, the width of the aperture transducer group, and a steering angle range of a scanning line. The display unit 34 displays the ultrasound image based on the image information data only in the display image region.

13 Claims, 5 Drawing Sheets

(56) References Cited

U.S. PATENT DOCUMENTS

| | | | |
|---|---|---|---|
| 2009/0069681 A1* | 3/2009 | Lundberg | G01S 15/8995 |
| | | | 600/463 |
| 2010/0160786 A1* | 6/2010 | Nordgren | A61B 8/461 |
| | | | 600/459 |
| 2012/0065509 A1* | 3/2012 | Ziv-Ari | G01S 7/52077 |
| | | | 600/443 |
| 2014/0350402 A1 | 11/2014 | Hirota et al. | |
| 2015/0272549 A1* | 10/2015 | Samset | G01S 7/52046 |
| | | | 600/443 |
| 2016/0367222 A1* | 12/2016 | Yamamoto | G01S 7/52047 |
| 2017/0071475 A1* | 3/2017 | Irisawa | A61B 1/07 |
| 2017/0296152 A1* | 10/2017 | Niemiec | A61B 8/5269 |
| 2018/0098750 A1* | 4/2018 | Haider | G01S 15/89 |

FOREIGN PATENT DOCUMENTS

| | | | |
|---|---|---|---|
| JP | 2003-230560 A | | 8/2003 |
| JP | 2003230560 A | * | 8/2003 |
| JP | 2005-087266 A | | 4/2005 |
| JP | 2013-188461 A | | 9/2013 |
| JP | 2014-097406 A | | 5/2014 |

OTHER PUBLICATIONS

Written Opinion issued in PCT/JP2019/016625; dated Jul. 16, 2019.
An Office Action; "Notice of Reasons for Refusal", mailed by the Japanese Patent Office dated Nov. 2, 2021, which corresponds to Japanese Patent Application No. 2020-516285 and is related to U.S. Appl. No. 17/060,206; with English language translation.

\* cited by examiner

ULTRASOUND SYSTEM AND METHOD FOR CONTROLLING ULTRASOUND SYSTEM

CROSS-REFERENCE TO RELATED APPLICATIONS

This application is a Continuation of PCT International Application No. PCT/JP2019/016625 filed on Apr. 18, 2019, which claims priority under 35 U.S.C. § 119(a) to Japanese Patent Application No. 2018-084305 filed on Apr. 25, 2018. The above application is hereby expressly incorporated by reference, in its entirety, into the present application.

BACKGROUND OF THE INVENTION

1. Field of the Invention

The present invention relates to an ultrasound system and a method for controlling the ultrasound system, and more particularly, to an ultrasound system that performs electronic sector scanning and a method for controlling the ultrasound system.

2. Description of the Related Art

An ultrasound diagnostic apparatus has been known as an apparatus for obtaining an image of the inside of a subject. In general, the ultrasound diagnostic apparatus comprises an ultrasound probe comprising a transducer array in which a plurality of ultrasound transducers is arranged. In a state in which the ultrasound probe comes into contact with the body surface of the subject, ultrasound beams are transmitted from the transducer array into the subject, and the transducer array receives ultrasound echoes from the subject to acquire element data. Further, the ultrasound diagnostic apparatus electrically processes the obtained element data to generate an ultrasound image of a corresponding part of the subject.

As an ultrasound beam scanning method, as disclosed in JP2002-224101A, there is a so-called electronic sector scanning method which gives a delay to transmission signals supplied to a plurality of ultrasound transducers and reception signals from the plurality of ultrasound transducers to change the angle of a scanning line.

SUMMARY OF THE INVENTION

In the ultrasound image obtained by the ultrasound probe of the electronic sector scanning type, the user needs to make an accurate diagnosis on the basis of the ultrasound image. Therefore, it is desirable to display a large observation range of the ultrasound image on a display unit of the ultrasound diagnostic apparatus. For example, in a portable ultrasound diagnostic apparatus, in many cases, a display screen of a display unit is smaller than a display screen of a display unit of a so-called stationary ultrasound diagnostic apparatus that is installed in, for example, an examination room and is then used. Therefore, the ultrasound image displayed on the display unit is small and it may be difficult for the user to make an accurate diagnosis on the basis of the ultrasound image.

The invention has been made in order to solve the problems and an object of the invention is to provide an ultrasound system and a method for controlling the ultrasound system that enable a user to make an accurate diagnosis on the basis of an ultrasound image.

In order to achieve the above object, according to the invention, there is provided an ultrasound system comprising an ultrasound probe and an image display device that are connected to each other, the ultrasound probe performing electronic sector scanning. The ultrasound probe includes: a transducer array in which a plurality of transducers are arranged in an arrangement direction; a transmitting and receiving unit that generates a sound ray signal by directing the ultrasound probe to transmit and receive ultrasonic waves using an aperture transducer group consisting of ultrasound transducers which are located in a central portion in the arrangement direction among the plurality of transducers and whose number is smaller than the number of the plurality of transducers; and an image information data generation unit that generates image information data on the basis of the sound ray signal generated by the transmitting and receiving unit. The image display device includes a display unit that displays an ultrasound image on the basis of the image information data generated by the image information data generation unit of the ultrasound probe. One of the ultrasound probe and the image display device includes a display image region determination unit that determines a display image region except a shallow image region which is located in a shallow depth range in the ultrasound image, on the basis of a width of the plurality of transducers in the arrangement direction, a width of the aperture transducer group in the arrangement direction, and a steering angle range in the electronic sector scanning. The display unit of the image display device displays the ultrasound image only in the display image region determined by the display image region determination unit.

In a case in which the width of the plurality of transducers in the arrangement direction is Wtr, the width of the aperture transducer group in the arrangement direction is Wap, and the steering angle range in the electronic sector scanning is Ast, the display image region determination unit may determine the display image region using, as the shallow image region, a region from an ultrasound transmitting and receiving surface of the transducer array to a depth Dcut represented by the following Expression (1) in the ultrasound image:

$$D\text{cut} = [(Wtr - Wap)/2] \times \tan[(180 - Ast)/2] \quad (1)$$

In this case, the shallow image region may have an isosceles trapezoidal shape having a lower base that has a length corresponding to the width Wtr, an upper base that has a length corresponding to the width Wap, and a height that corresponds to the depth Dcut.

The display image region determination unit may be provided in the ultrasound probe. The image information data of only the display image region determined by the display image region determination unit may be transmitted from the ultrasound probe to the image display device.

Alternatively, the display image region determination unit may be provided in the image display device. The ultrasound image may be displayed on the display unit on the basis of the image information data of only the display image region determined by the display image region determination unit in the image information data transmitted from the ultrasound probe to the image display device.

Preferably, the image information data is a signal obtained by performing attenuation correction according to a depth of a reflection position of the ultrasonic waves and an envelope detection process on the sound ray signal generated by the transmitting and receiving unit.

Alternatively, the image information data may be an ultrasound image signal obtained by performing attenuation correction according to a depth of a reflection position of the ultrasonic waves and an envelope detection process on the sound ray signal generated by the transmitting and receiving unit and converting the sound ray signal according to a predetermined image display method.

Preferably, the transmitting and receiving unit includes: a transmitting unit that directs the transducer array to transmit the ultrasonic waves; and a receiving unit that generates the sound ray signal on the basis of a reception signal acquired by the transducer array.

According to the invention, there is provided a method for controlling an ultrasound system in which an ultrasound probe that performs electronic sector scanning and an image display device are connected. The method comprises: generating a sound ray signal by performing transmission and reception of ultrasonic waves using an aperture transducer group consisting of ultrasound transducers which are located in a central portion in an arrangement direction among a plurality of transducers arranged in a transducer array of the ultrasound probe and whose number is smaller than the number of the plurality of transducers; generating image information data on the basis of the generated sound ray signal; transmitting the generated image information data from the ultrasound probe to the image display device; determining a display image region except a shallow image region which is located in a shallow depth range in the ultrasound image, on the basis of a width of the plurality of transducers in the arrangement direction, a width of the aperture transducer group in the arrangement direction, and a steering angle range in the electronic sector scanning; and displaying the ultrasound image only in the determined display image region on a display unit of the image display device on the basis of the image information data generated by the ultrasound probe.

According to the invention, one of the ultrasound probe and the image display device includes the display image region determination unit that determines the display image region except the shallow image region located in the shallow depth range, in which an ultrasound dead zone is formed, in the ultrasound image, on the basis of the width of the plurality of transducers in the arrangement direction, the width of the aperture transducer group in the arrangement direction, and the steering angle range in the electronic sector scanning. The display unit of the image display device displays the ultrasound image only in the display image region determined by the display image region determination unit. Therefore, the user can make an accurate diagnosis on the basis of the ultrasound image.

DESCRIPTION OF THE PREFERRED EMBODIMENTS

Embodiments of the invention will be described below with reference to the accompanying drawings.

Embodiment 1

Figure 1:
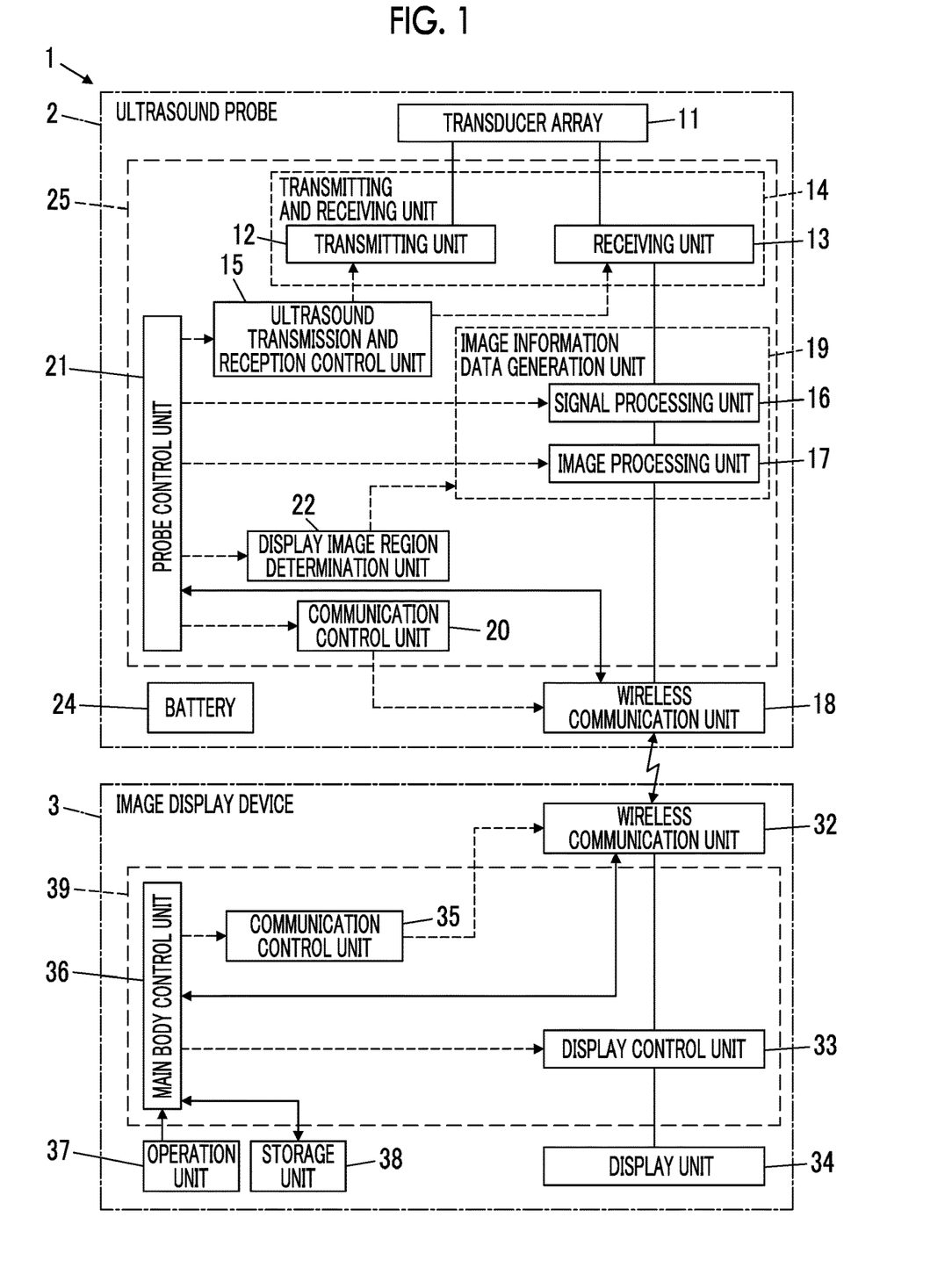
FIG. 1 is a block diagram illustrating a configuration of an ultrasound system according to Embodiment 1 of the invention.

FIG. 1 illustrates the configuration of an ultrasound system 1 according to Embodiment 1 of the invention. As illustrated in FIG. 1, the ultrasound system 1 comprises an ultrasound probe 2 and an image display device 3. The ultrasound probe 2 and the image display device 3 are connected by wireless communication.

The ultrasound probe 2 of the ultrasound system 1 comprises a transducer array 11. The transducer array 11 is connected to a transmitting unit 12 and a receiving unit 13. The transmitting unit 12 and the receiving unit 13 form a transmitting and receiving unit 14. An ultrasound transmission and reception control unit 15 is connected to the transmitting unit 12 and the receiving unit 13. A signal processing unit 16, an image processing unit 17, and a wireless communication unit 18 are sequentially connected to the receiving unit 13. The signal processing unit 16 and the image processing unit 17 form an image information data generation unit 19.

In addition, a communication control unit 20 is connected to the wireless communication unit 18, and a display image region determination unit 22 is connected to the image information data generation unit 19. Further, a probe control unit 21 is connected to the ultrasound transmission and reception control unit 15, the signal processing unit 16, the image processing unit 17, the communication control unit 20, and the display image region determination unit 22. Further, the ultrasound probe 2 has a battery 24 provided therein.

A probe-side processor 25 is configured by the transmitting unit 12, the receiving unit 13, the ultrasound transmission and reception control unit 15, the signal processing unit 16, the image processing unit 17, the communication control unit 20, the probe control unit 21, and the display image region determination unit 22.

The image display device 3 of the ultrasound system 1 comprises a wireless communication unit 32. A display control unit 33 and a display unit 34 are sequentially connected to the wireless communication unit 32. Further, a communication control unit 35 is connected to the wireless communication unit 32. Furthermore, a main body control unit 36 is connected to the display control unit 33 and the communication control unit 35. An operation unit 37 and a storage unit 38 are connected to the main body control unit 36. The wireless communication unit 32 and the main body control unit 36 are connected such that information can be bidirectionally received and transmitted. The main body control unit 36 and the storage unit 38 are connected such that information can be bidirectionally received and transmitted.

Furthermore, a display-device-side processor 39 is configured by the display control unit 33, the communication control unit 35, and the main body control unit 36.

Further, the wireless communication unit 18 of the ultrasound probe 2 and the wireless communication unit 32 of the image display device 3 are connected such that information can be bidirectionally received and transmitted. Therefore, the ultrasound probe 2 and the image display device 3 are connected by wireless communication.

Figure 2:
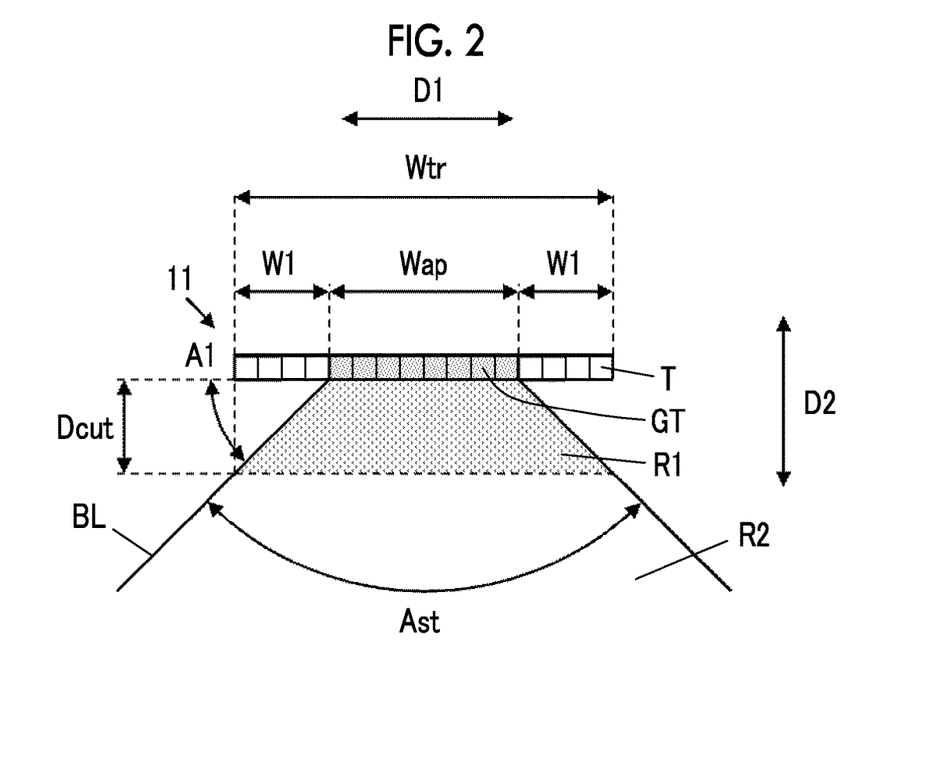
FIG. 2 is a diagram schematically illustrating a shallow image region in electronic sector scanning.

The transducer array 11 of the ultrasound probe 2 has a plurality of ultrasound transducers which are arranged one-dimensionally or two-dimensionally. For example, as illustrated in FIG. 2, a plurality of ultrasound transducers T can be one-dimensionally arranged along an arrangement direction D1. Each of the transducers transmits ultrasonic waves according to a driving voltage supplied from the transmitting unit 12, receives waves reflected from a subject, and outputs a reception signal. Each transducer is configured using an element in which electrodes are formed at both ends of a piezoelectric body consisting of, for example, a piezoelectric ceramic typified by lead zirconate titanate (PZT), a polymeric piezoelectric element typified by polyvinylidene difluoride (PVDF), and a piezoelectric single crystal typified by lead magnesium niobate-lead titanate (PMN-PT).

The ultrasound transmission and reception control unit 15 of the probe-side processor 25 controls the transmitting unit 12 and the receiving unit 13 of the transmitting and receiving unit 14 to perform the transmission of ultrasound beams and the reception of ultrasound echoes on the basis of an electronic sector scanning method and an inspection mode instructed by the probe control unit 21.

In this case, the ultrasound transmission and reception control unit 15 controls the transmitting and receiving unit 14 such that the ultrasound probe 2 transmits and receives ultrasonic waves using an aperture transducer group GT consisting of the ultrasound transducers T, which are located in a central portion in the arrangement direction D1 of the ultrasound transducers T among the plurality of ultrasound transducers T forming the transducer array 11 and are used as ultrasound transmission and reception channels and whose number is smaller than the total number of the plurality of ultrasound transducers T, as illustrated in FIG. 2. For example, in a case in which the transducer array 11 includes 64 ultrasound transducers T, the ultrasound transmission and reception control unit 15 can control the transmitting and receiving unit 14 such that the aperture transducer group GT consisting of 32 ultrasound transducers T which are located in the central portion in the arrangement direction D1 of the ultrasound transducers T transmits and receives ultrasonic waves. As described above, in the invention, the ultrasound transducers T whose number is smaller than the total number of the plurality of ultrasound transducers T are used as the ultrasound transmission and reception channels. Therefore, it is possible to reduce the power consumption of the ultrasound probe 2.

For example, in a portable ultrasound system that is driven by a battery as a power source, the magnitude of power consumption has a large effect on the continuous use time of the ultrasound system. Therefore, power consumption in the battery can be reduced by setting the number of ultrasound transducers used as the transmission channels and the reception channels used to transmit and receive ultrasonic waves to be smaller than the total number of ultrasound transducers included in the ultrasound probe of the ultrasound system.

The transmitting unit 12 of the transmitting and receiving unit 14 includes, for example, a plurality of pulse generators, adjusts the amount of delay of each driving voltage on the basis of a transmission delay pattern selected according to a control signal from the ultrasound transmission and reception control unit 15 such that the ultrasonic waves transmitted from the plurality of transducers of the transducer array 11 form an ultrasound beam, and supplies the driving voltages to the plurality of transducers. As such, in a case in which a pulsed or continuous-wave voltage is applied to the electrodes of the transducers of the transducer array 11, the piezoelectric body is expanded and contracted and pulsed or continuous ultrasonic waves are generated from each transducer. An ultrasound beam is formed from a combined wave of the ultrasonic waves.

The transmitted ultrasound beam is propagated in the subject along a scanning line within a predetermined steering angle range Ast as illustrated in FIG. 2. In this case, the transmitting unit 12 transmits ultrasound beams into the subject while changing the inclination of the scanning line within the steering angle range Ast according to a control signal from the ultrasound transmission and reception control unit 15. Here, the steering angle range Ast is set so as to be bilaterally symmetric in the arrangement direction D1 of the plurality of ultrasound transducers T. For example, the steering angle range Ast is set to a maximum of 90 degrees.

The ultrasound beam transmitted in the subject is reflected by a target, such as a part of the subject, and is propagated toward the transducer array 11. The ultrasonic waves propagated toward the transducer array 11 in this way are received by each of the ultrasound transducers forming the transducer array 11. In this case, each of the ultrasound transducers forming the transducer array 11 receives propagated ultrasound echoes, is expanded and contracted to generate an electric signal, and outputs a reception signal which is the electric signal to the receiving unit 13.

Figure 3:
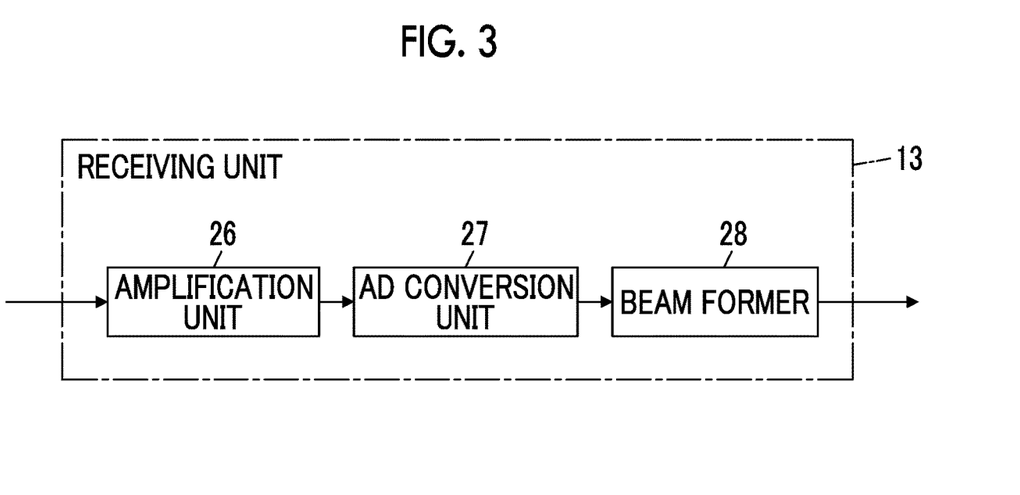
FIG. 3 is a block diagram illustrating an internal configuration of a receiving unit according to Embodiment 1 of the invention.

The receiving unit 13 of the transmitting and receiving unit 14 processes the reception signal output from the transducer array 11 according to a control signal from the ultrasound transmission and reception control unit 15. As illustrated in FIG. 3, the receiving unit 13 has a configuration in which an amplification unit 26, an analog digital (AD) conversion unit 27, and a beam former 28 are connected in series to each other. The amplification unit 26 amplifies the reception signal input from each of the transducers forming the transducer array 11 and transmits the amplified reception signal to the AD conversion unit 27. The AD conversion unit 27 converts the reception signal transmitted from the amplification unit 26 into digital element data and transmits the element data to the beam former 28. The beam former 28 performs a reception focusing process which gives a delay to each element data item following the set sound velocity on the basis of a reception delay pattern selected according to a control signal from the ultrasound transmission and reception control unit 15 and performs addition (phasing addition). The sound ray signal in which the focus of the ultrasound echo is narrowed down on a certain scanning line is generated by the reception focusing process.

The inventors have found that a region as an ultrasound dead zone is generated and this region hinders the display of various kinds of information on the display unit in a case in which an aperture transducer group G consisting of the ultrasound transducers T whose number is smaller than the total number of the plurality of ultrasound transducers T is used in an ultrasound probe of an electronic sector scanning type, that is, in a case in which the number of ultrasound transducers used as the transmission channels and the reception channels is smaller than the total number of ultrasound transducers included in the ultrasound probe.

Here, as illustrated in FIG. 2, in a case in which the plurality of ultrasound transducers T forming the transducer array 11 of the ultrasound probe 2 receive the ultrasound echoes, the plurality of ultrasound transducers T generally vibrates in a vertical direction D2 perpendicular to the arrangement direction D1 of the plurality of ultrasound transducers T to generate an electric signal, thereby generating a reception signal. Therefore, for example, the ultrasound echoes from a shallow region of the subject which is out of the steering angle range Ast and is close to the transducer array 11 have a large number of components along the arrangement direction D1 and has a small number of components along the vertical direction D2. As a result, the vibration of the ultrasound transducer T due to the ultrasound echoes is reduced. Therefore, the intensity of the reception signal caused by the ultrasound echoes from the shallow region of the subject is likely to be very low. In the following description, the range in which the intensity of the reception signal is very low is referred to as an ultrasound dead zone. In general, in a case in which a user such, as a doctor, makes a diagnosis of the subject with reference to an ultrasound image, a region which is located in a shallow depth range including the ultrasound dead zone in the ultrasound image is not useful and is not referred to.

As illustrated in FIG. 2, the display image region determination unit 22 of the probe-side processor 25 according to Embodiment 1 of the invention determines a display image region R2 except a shallow image region R1 located in the shallow depth range in which the ultrasound dead zone is formed in the ultrasound image. Here, for example, in a case in which the transducer array 11 is configured by 64 ultrasound transducers T, the total width of the 64 ultrasound transducers T in the arrangement direction D1 is generally about 2 cm. Further, in the invention, the aperture transducer group GT consisting of some ultrasound transducers T which are located in the central portion in the arrangement direction D1 among the plurality of ultrasound transducers T forming the transducer array 11 is used to transmit and receive ultrasonic waves. Therefore, at least the ultrasound dead zone is included in shallow depth range having a depth Dcut from both ends of the transducer array 11 in the arrangement direction D1 to a boundary line BL between the inside and the outside of the steering angle range Ast.

Specifically, as illustrated in FIG. 2, it is assumed that a length from one end of the aperture transducer group GT in the arrangement direction D1 to one end of the transducer array 11 in the arrangement direction D1, that is, the width of an ultrasound transducer group which is located on both sides of the aperture transducer group GT and is not used to transmit and receive ultrasonic waves is W1, and an angle formed between a direction along the boundary line BL between the inside and the outside of the steering angle range Ast and the arrangement direction D1 of the plurality of ultrasound transducers T is A1. The display image region determination unit 22 calculates a region up to the depth Dcut represented by the following Expression (1) as the shallow image region R1 using the width W1 and the angle A1 and determines the display image region R2 except the calculated shallow image region R1 in the ultrasound image. This makes it possible to remove a portion that is not useful for diagnosis in the ultrasound image.

$$Dcut = W1 \times \tan(A1) \quad (1)$$

In a case in which the total width Wtr of the plurality of ultrasound transducers T in the arrangement direction D1, an aperture width Wap which is the length of the aperture transducer group GT in the arrangement direction D1, and the steering angle range Ast in electronic sector scanning are known, the width W1 in Expression (1) is represented by the following Expression (2) and the angle A1 is represented by the following Expression (3).

$$W1 = (Wtr - Wap)/2 \quad (2)$$

$$A1 = (180 - Ast)/2 \quad (3)$$

Therefore, Expression (1) can be calculated as the following Expression (4).

$$Dcut = [(Wtr - Wap)/2] \times \tan[(180 - Ast)/2] \quad (4)$$

Here, in the example illustrated in FIG. 2, the shallow image region R1 has an isosceles trapezoidal shape having a lower base that has a length corresponding to the total width Wtr of the plurality of ultrasound transducers T, an upper base that has a length corresponding to the aperture width Wap of the aperture transducer group GT, and a height that corresponds to the depth Dcut.

The image information data generation unit 19 generates image information data corresponding to only the display image region R2 determined by the display image region determination unit 22 and transmits the generated image information data to the wireless communication unit 18.

Here, the signal processing unit 16 of the image information data generation unit 19 corrects the attenuation of the sound ray signal generated by the beam former 28 of the receiving unit 13 caused by a propagation distance according to the depth of the position where the ultrasonic waves are reflected and performs an envelope detection process on the sound ray signal to generate a signal which is tomographic image information related to the tissues in the subject.

The image processing unit 17 of the image information data generation unit 19 raster-converts the signal generated by the signal processing unit 16 into an image signal following a general television signal scanning method, and performs various types of necessary image processing, such as brightness correction, gradation correction, sharpness correction, and color correction, on the generated image signal to generate an ultrasound image signal. In this case, for example, the image processing unit 17 can remove a portion corresponding to the shallow image region R1 from the ultrasound image signal on the basis of the display image region R2 determined by the display image region determination unit 22. Further, the image processing unit 17 transmits the generated ultrasound image signal to the wireless communication unit 18 of the ultrasound probe 2.

The wireless communication unit 18 of the ultrasound probe 2 includes an antenna for transmitting and receiving radio waves and performs wireless communication with the wireless communication unit 32 of the image display device 3. In this case, the wireless communication unit 18 modulates a carrier on the basis of the ultrasound image signal of only the display image region R2 generated by the image processing unit 17 of the image information data generation unit 19 to generate a transmission signal and wirelessly transmits the generated transmission signal to the wireless communication unit 32 of the image display device 3. For example, amplitude shift keying (ASK), phase shift keying (PSK), quadrature phase shift keying (QPSK), and 16 quadrature amplitude modulation (16 QAM) are used as the carrier modulation method.

The communication control unit 20 of the probe-side processor 25 controls the wireless communication unit 18 of the ultrasound probe 2 such that the ultrasound image signal is transmitted with transmission radio field intensity set by the probe control unit 21.

The probe control unit 21 of the probe-side processor 25 controls each unit of the ultrasound probe 2 on the basis of, for example, a program stored in advance.

The battery 24 of the ultrasound probe 2 is provided in the ultrasound probe 2 and supplies power to each circuit of the ultrasound probe 2.

The wireless communication unit 32 of the image display device 3 includes an antenna for transmitting and receiving radio waves and performs wireless communication with the wireless communication unit 18 of the ultrasound probe 2. In this case, the wireless communication unit 32 of the image display device 3 receives, for example, the transmission signal wirelessly transmitted from the wireless communication unit 18 of the ultrasound probe 2 through the antenna, demodulates the received transmission signal, outputs the ultrasound image signal, and transmits the output ultrasound image signal to the display control unit 33.

The display control unit 33 of the display-device-side processor 39 performs predetermined processing on the ultrasound image signal demodulated by the wireless communication unit 32 and displays an ultrasound image on the display unit 34 under the control of the main body control unit 36.

Figure 4:
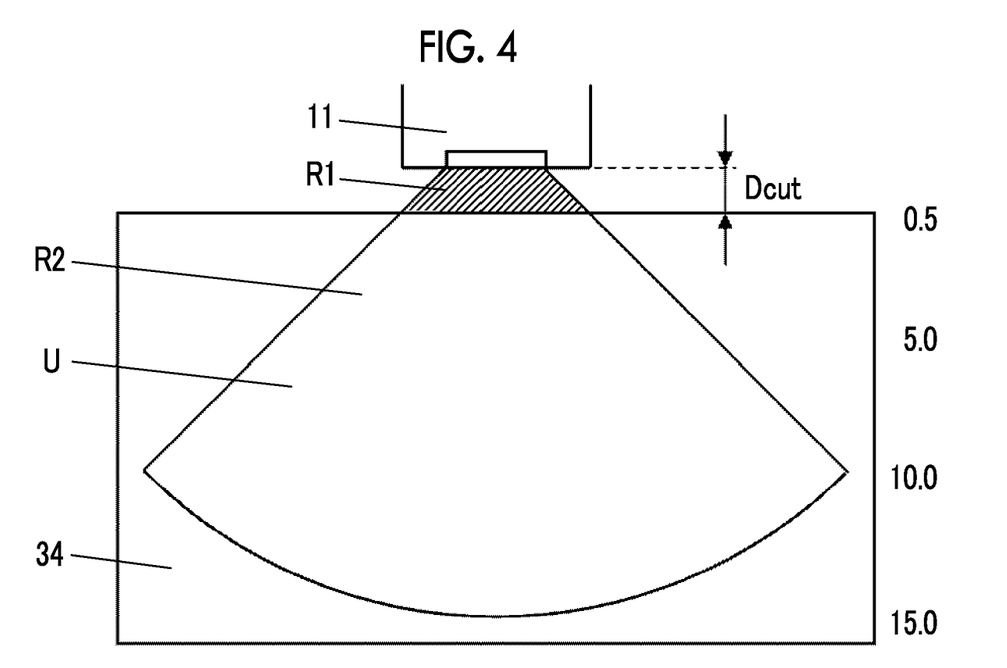
FIG. 4 is a diagram schematically illustrating a display image region in the electronic sector scanning.

The display unit 34 of the image display device 3 includes a display device, such as a liquid crystal display (LCD), and displays the image generated by the display control unit 33. In this case, the display unit 34 displays an ultrasound image U only in the display image region R2 determined by the display image region determination unit 22 as illustrated in FIG. 4. For example, in a case in which the depth Dcut of the shallow image region R1 is 0.5 cm, the display unit 34 displays the ultrasound image U not from a depth of 0 cm but from a depth of 0.5 cm to a predetermined depth as illustrated in FIG. 4. As such, the display unit 34 does not display the shallow image region R1 having the depth Dcut from the transducer array 11, which is not useful for diagnosis by a user such as a doctor. Therefore, it is possible to display the display image region R2 with a relatively large size.

The communication control unit 35 of the display-device-side processor 39 controls the wireless communication unit 32 of the image display device 3 such that the transmission signal is received from the wireless communication unit 18 of the ultrasound probe 2.

The main body control unit 36 of the display-device-side processor 39 controls each unit of the image display device 3 on the basis of the program stored in advance in, for example, the storage unit 38 and the operation of the user input through the operation unit 37.

The operation unit 37 of the image display device 3 is used by the user to perform an input operation and can be configured to comprise, for example, a keyboard, a mouse, a trackball, a touch pad, and a touch panel.

The storage unit 38 of the image display device 3 stores, for example, an operation program for the image display device 3. The following can be used as the storage unit 38: a recording medium, such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), or a sever.

Here, the probe-side processor 25 including the transmitting and receiving unit 14, the ultrasound transmission and reception control unit 15, the image information data generation unit 19, the communication control unit 20, the probe control unit 21, and the display image region determination unit 22 in the ultrasound probe 2 and the display-device-side processor 39 including the display control unit 33, the communication control unit 35, and the main body control unit 36 in the image display device 3 are implemented by a central processing unit (CPU) and a control program for causing the CPU to perform various processes. However, the processors may be implemented by a field programmable gate array (FPGA), a digital signal processor (DSP), an application specific integrated circuit (ASIC), a graphics processing unit (GPU), other integrated circuits (ICs), or combinations thereof.

Some or all of the transmitting and receiving unit 14, the ultrasound transmission and reception control unit 15, the image information data generation unit 19, the communication control unit 20, the probe control unit 21, and the display image region determination unit 22 of the probe-side processor 25 may be integrated into, for example, one CPU. Similarly, some or all of the display control unit 33, the communication control unit 35, and the main body control unit 36 of the display-device-side processor 39 may be integrated into, for example, one CPU.

As described above, according to the ultrasound system 1 of Embodiment 1 of the invention, the display image region determination unit 22 determines the display image region R2 except the shallow image region R1 located in the shallow depth range in which the ultrasound dead zone is formed in the ultrasound image, and the display unit 34 displays the ultrasound image only in the display image region R2 that is useful for diagnosis. Therefore, the user can make an accurate diagnosis on the basis of the ultrasound image.

In Embodiment 1, the configuration has been described in which the image processing unit 17 of the image information data generation unit 19 excludes a portion corresponding to the shallow image region R1 from the ultrasound image signal. However, the signal processing unit 16 may perform the process of excluding the shallow image region R1. In this case, for example, the signal processing unit 16 can remove the portion corresponding to the shallow image region R1 from the signal subjected to an envelope detection process. Further, for example, the signal processing unit 16 can exclude the portion corresponding to the shallow image region R1 from the sound ray signal generated by the receiving unit 13 of the transmitting and receiving unit 14.

The steering angle range Ast may be set by the user through the operation unit 37 of the image display device 3. In this case, a command to change the steering angle range Ast which is input by the user through the operation unit 37 is wirelessly transmitted to the ultrasound probe 2 through the wireless communication unit 32 of the image display device 3. The ultrasound transmission and reception control unit 15 of the probe-side processor 25 controls the transmitting and receiving unit 14 on the basis of the wirelessly transmitted command such that the transducer array 11 transmits and receives ultrasonic waves on the basis of the steering angle range Ast set by the user through the operation unit 37 of the image display device 3.

In addition, in a case in which the ultrasound probe 2 is provided with an operation unit, the ultrasound transmission and reception control unit 15 controls the transmitting and receiving unit 14 such that ultrasonic waves are transmitted and received on the basis of the steering angle range set by the user through the operation unit of the ultrasound probe 2, which is not illustrated.

Further, the steering angle range Ast may be appropriately changed and the depth Dcut of the shallow image region R1 may be calculated using the changed steering angle range Ast. In this case, the value of the depth Dcut of the shallow image region R1 calculated by Expression (4) becomes larger as the steering angle range Ast becomes narrower and becomes smaller as the steering angle range Ast becomes wider. Therefore, the depth range of the display image region R2 is determined according to the width of the steering angle range Ast, and only a portion that is more useful for diagnosis in the ultrasound image is displayed on the display unit 34. Therefore, the user can make a more accurate diagnosis.

In Embodiment 1, the ultrasound probe 2 and the image display device 3 are wirelessly connected to each other by the wireless communication unit 18 of the ultrasound probe 2 and the wireless communication unit 32 of the image display device 3. However, they may be connected to each other in a wired manner. For example, each of the ultrasound probe 2 and the image display device 3 may be provided with a connection terminal to which a cable capable of transmitting information can be connected. The connection terminals may be connected to each other by the cable to connect the ultrasound probe 2 and the image display device 3 in a wired manner. Further, in Embodiment 1, as the ultrasound system 1, the portable (mobile) ultrasound system has been described an example. However, Embodiment 1 may be applied to stationary ultrasound systems. Similarly, the following Embodiments 2 and 3 may be applied to the stationary ultrasound systems.

Embodiment 2

Figure 5:
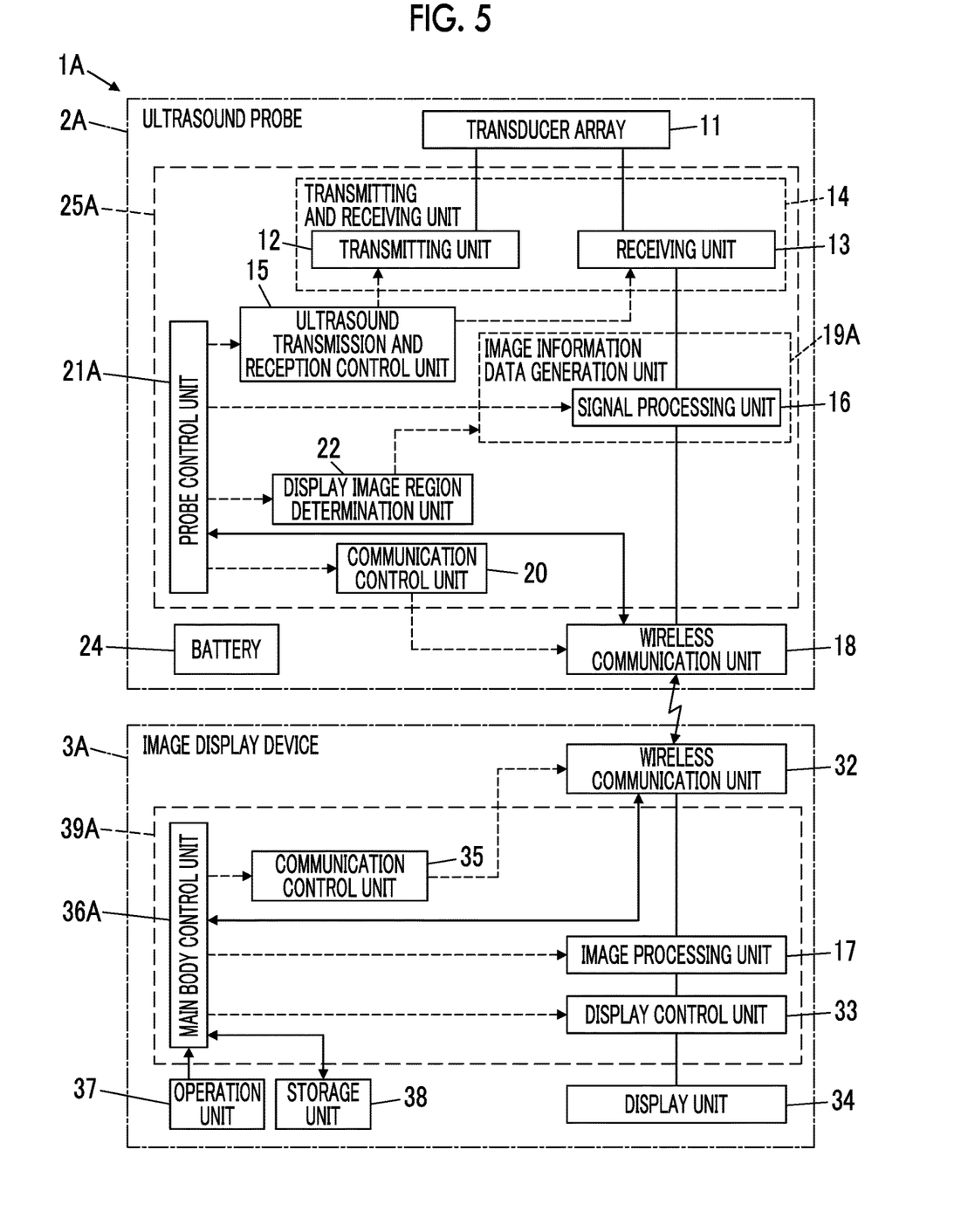
FIG. 5 is a block diagram illustrating a configuration of an ultrasound system according to Embodiment 2 of the invention.

As illustrated in FIG. 5, an ultrasound system 1A according to Embodiment 2 comprises an ultrasound probe 2A and an image display device 3A. The ultrasound probe 2A according to Embodiment 2 is different from the ultrasound probe 2 according to Embodiment 1 illustrated in FIG. 1 in that the image processing unit 17 is removed and a probe control unit 21A is provided instead of the probe control unit 21.

The image display device 3A according to Embodiment 2 is different from the image display device 3 according to Embodiment 1 illustrated in FIG. 1 in that the image processing unit 17 is added and a main body control unit 36A is provided instead of the main body control unit 36. The image processing unit 17 comprised in the image display device 3A in Embodiment 2 is the same as the image processing unit 17 comprised in the ultrasound probe 2 in Embodiment 1 illustrated in FIG. 1.

As illustrated in FIG. 5, in the ultrasound probe 2A, the wireless communication unit 18 is directly connected to the signal processing unit 16, and an image information data generation unit 19A is configured by the signal processing unit 16. In addition, the probe control unit 21A is connected to the ultrasound transmission and reception control unit 15, the signal processing unit 16, the wireless communication unit 18, the communication control unit 20, and the display image region determination unit 22. Further, a probe-side processor 25A is configured by the transmitting and receiving unit 14, the ultrasound transmission and reception control unit 15, the signal processing unit 16, the communication control unit 20, the probe control unit 21A, and the display image region determination unit 22.

In the image display device 3A, the image processing unit 17, the display control unit 33, and the display unit 34 are sequentially connected to the wireless communication unit 32. Further, a main body control unit 36A is connected to the image processing unit 17, the wireless communication unit 32, the display control unit 33, the communication control unit 35, the operation unit 37, and the storage unit 38. Furthermore, a display-device-side processor 39A is configured by the image processing unit 17, the display control unit 33, the communication control unit 35, and the main body control unit 36A.

The image information data generation unit 19A of the probe-side processor 25A, that is, the signal processing unit 16 generates a signal subjected to the envelope detection process as image information data corresponding to only the display image region R2 determined by the display image region determination unit 22. Specifically, the signal processing unit 16 performs attenuation correction and the envelope detection process on the sound ray signal generated by the receiving unit 13 of the transmitting and receiving unit 14 on the basis of the display image region R2 determined by the display image region determination unit 22 to generate a signal corresponding to only the display image region R2. The signal processing unit 16 transmits the generated signal to the wireless communication unit 18 of the ultrasound probe 2A as the image information data.

The wireless communication unit 18 of the ultrasound probe 2A modulates a carrier on the basis of the signal generated by the signal processing unit 16 to generate a transmission signal and wirelessly transmits the generated transmission signal to the wireless communication unit 32 of the image display device 3A.

The wireless communication unit 32 of the image display device 3A demodulates the transmission signal wirelessly transmitted from the wireless communication unit 18 of the ultrasound probe 2A and transmits the demodulated signal to the image processing unit 17 of the display-device-side processor 39A.

The image processing unit 17 of the display-device-side processor 39A raster-converts the signal transmitted from the wireless communication unit 32 into an image signal following the general television signal scanning method, performs various types of necessary image processing, such as brightness correction, gradation correction, sharpness correction, and color correction, on the generated image signal to generate an ultrasound image signal, and transmits the ultrasound image signal to the display control unit 33.

The display control unit 33 of the display-device-side processor 39A performs predetermined processing on the ultrasound image signal transmitted from the image processing unit 17 and displays an ultrasound image on the display unit 34 under the control of the main body control unit 36A.

The display unit 34 of the image display device 3A displays the image generated by the display control unit 33. In this case, the display unit 34 displays the ultrasound image U only in the display image region R2 determined by the display image region determination unit 22 of the probe-side processor 25A as illustrated in FIG. 4.

As described above, according to the ultrasound system 1A of Embodiment 2 of the invention, even in a case in which the image processing unit 17 is not provided in the ultrasound probe 2A, but is provided in the image display device 3A, similar to Embodiment 1, the display image region determination unit 22 determines the display image region R2 except the shallow image region R1 located in the shallow depth range in which the ultrasound dead zone is formed in the ultrasound image, and the display unit 34 displays the ultrasound image only in the display image region R2 that is useful for diagnosis. Therefore, the user can make an accurate diagnosis on the basis of the ultrasound image.

Embodiment 3

Figure 6:
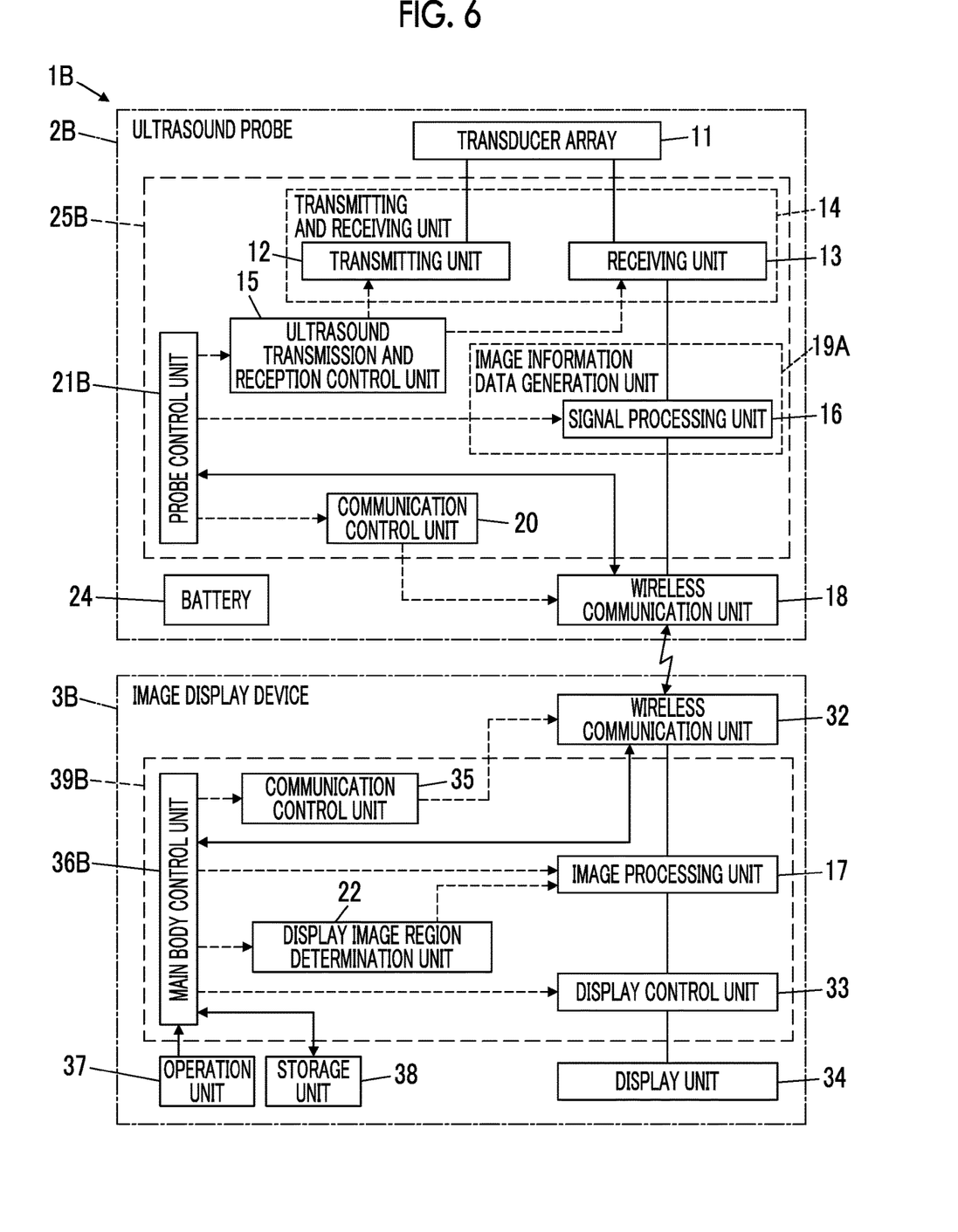
FIG. 6 is a block diagram illustrating a configuration of an ultrasound system according to Embodiment 3 of the invention.

As illustrated in FIG. 6, an ultrasound system 1B according to Embodiment 3 comprises an ultrasound probe 2B and an image display device 3B. The ultrasound probe 2B according to Embodiment 3 is different from the ultrasound probe 2 according to Embodiment 1 illustrated in FIG. 1 in that the image processing unit 17 and the display image region determination unit 22 are removed and a probe control unit 21B is provided instead of the probe control unit 21.

The image display device 3B according to Embodiment 3 is different from the image display device 3 according to Embodiment 1 illustrated in FIG. 1 in that the image processing unit 17 and the display image region determination unit 22 are added and a main body control unit 36B is provided instead of the main body control unit 36. Here, the image processing unit 17 and the display image region determination unit 22 comprised in the image display device 3B are the same as the image processing unit 17 and the display image region determination unit 22 in Embodiment 1 illustrated in FIG. 1, respectively.

As illustrated in FIG. 6, in the ultrasound probe 2B, the signal processing unit 16 is connected to the wireless communication unit 18 and an image information data generation unit 19A is configured by the signal processing unit 16. Further, the probe control unit 21B is connected to the ultrasound transmission and reception control unit 15, the signal processing unit 16, the wireless communication unit 18, and the communication control unit 20. Furthermore, a probe-side processor 25B is configured by the transmitting and receiving unit 14, the ultrasound transmission and reception control unit 15, the signal processing unit 16, the communication control unit 20, and the probe control unit 21B.

Further, in the image display device 3B, the image processing unit 17, the display control unit 33, and the display unit 34 are sequentially connected to the wireless communication unit 32, and the display image region determination unit 22 is connected to the image processing unit 17. Further, the main body control unit 36B is connected to the image processing unit 17, the display image region determination unit 22, the wireless communication unit 32, the display control unit 33, the communication control unit 35, the operation unit 37, and the storage unit 38. Furthermore, a display-device-side processor 39B is configured by the image processing unit 17, the display image region determination unit 22, the display control unit 33, the communication control unit 35, and the main body control unit 36B.

The image information data generation unit 19A of the probe-side processor 25B, that is, the signal processing unit 16 performs attenuation correction and the envelope detection process on the sound ray signal generated by the receiving unit 13 of the transmitting and receiving unit 14 to generate a signal which is tomographic image information related to the tissues in the subject. The signal processing unit 16 transmits the generated signal to the wireless communication unit 18 of the ultrasound probe 2B as image information data.

The wireless communication unit 18 of the ultrasound probe 2B modulates a carrier on the basis of the signal generated by the signal processing unit 16 to generate a transmission signal and wirelessly transmits the generated transmission signal to the wireless communication unit 32 of the image display device 3B.

The wireless communication unit 32 of the image display device 3B demodulates the transmission signal wirelessly transmitted from the wireless communication unit 18 of the ultrasound probe 2B and transmits the demodulated signal to the image processing unit 17 of the display-device-side processor 39B.

The display image region determination unit 22 of the display-device-side processor 39B determines the display image region R2 except the shallow image region R1 located in the shallow depth range in which the ultrasound dead zone is formed in the ultrasound image, as illustrated in FIG. 2. In this case, the display image region determination unit 22 calculates the depth Dcut of the shallow image region R1 using Expression (1) or Expression (4).

The image processing unit 17 of the display-device-side processor 39B generates an ultrasound image signal corresponding to only the display image region R2 from the signal transmitted from the wireless communication unit 32 of the image display device 3B on the basis of the display image region R2 determined by the display image region determination unit 22 and transmits the generated ultrasound image signal to the display control unit 33.

The display control unit 33 of the display-device-side processor 39B performs predetermined processing on the ultrasound image signal transmitted from the image processing unit 17 and displays an ultrasound image on the display unit 34 under the control of the main body control unit 36B.

The display unit 34 of the image display device 3B displays the image generated by the display control unit 33. In this case, the display unit 34 displays the ultrasound image U only in the display image region R2 determined by the display image region determination unit 22 of the display-device-side processor 39B, as illustrated in FIG. 4.

As described above, according to the ultrasound system 1B of Embodiment 3 of the invention, even in a case in which the display image region determination unit 22 is not provided in the ultrasound probe 2B, but is provided in the image display device 3B, similar to Embodiments 1 and 2, the display image region determination unit 22 determines the display image region R2 except the shallow image region R1 located in the shallow depth range in which the ultrasound dead zone is formed in the ultrasound image, and the display unit 34 displays the ultrasound image only in the display image region R2 that is useful for diagnosis. Therefore, the user can make an accurate diagnosis on the basis of the ultrasound image.

EXPLANATION OF REFERENCES 1, 1A, 1B: ultrasound system
2, 2A, 2B: ultrasound probe
3, 3A, 3B: image display device
11: transducer array
12: transmitting unit
13: receiving unit
14: transmitting and receiving unit
15: ultrasound transmission and reception control unit
16: signal processing unit
17: image processing unit
18, 32: wireless communication unit
19, 19A: image information data generation unit
20, 35: communication control unit
21, 21A, 21B: probe control unit
22: display image region determination unit
24: battery
25, 25A, 25B: probe-side processor
26: amplification unit
27: AD conversion unit
28: beam former
33: display control unit
34: display unit
36, 36A, and 36B: main body control unit
37: operation unit
38: storage unit
39, 39A, 39B: display-device-side processor A1: angle
Ast: steering angle range
BL: boundary line
D1: arrangement direction
D2: vertical direction
Dcut: depth
GT: aperture transducer group
R1: shallow image region
R2: display image region
T: ultrasound transducer
U: ultrasound image
W1: width
Wap: aperture width
Wtr: total width.

What is claimed is:

1. An ultrasound system comprising:
a portable ultrasound probe, which is driven by a battery, and an image display device that are connected to each other, the portable ultrasound probe performing electronic sector scanning,
wherein the portable ultrasound probe includes:
a transducer array in which a plurality of transducers are arranged in an arrangement direction; and
a processor configured to
generate a sound ray signal by directing the portable ultrasound probe to transmit and receive ultrasonic waves using an aperture transducer group consisting of ultrasound transducers which are located in a central portion in the arrangement direction among the plurality of transducers and whose number is smaller than the number of the plurality of transducers,
generate image information data based on the sound ray signal, and
determine a display image region except a shallow image region including an ultrasound dead zone and having an isosceles trapezoidal shape,
the ultrasound dead zone is a region in which an intensity of an ultrasound echo in the arrangement direction is larger than the intensity of the ultrasound echo in a vertical direction perpendicular to the arrangement direction and is located in a shallow depth range and out of the steering angle in the ultrasound image,
the isosceles trapezoidal shape has a lower base which has a length corresponding to the total width of the plurality of transducers in the arrangement direction, an upper base which has a length corresponding to the width of the aperture transducer group in the arrangement direction, and a height which corresponds to a depth from both ends of the transducer array in the arrangement direction to a boundary line between an inside and an outside of a steering angle range in the electronic sector scanning,
the image display device includes a display unit configured to display the ultrasound image based on the image information data generated by the processor in the portable ultrasound probe, and
the display unit of the image display device is further configured to display the ultrasound image only in the display image region determined by the processor in the portable ultrasound probe.

2. The ultrasound system according to claim 1,
wherein, in a case in which the width of the plurality of transducers in the arrangement direction is Wtr, the width of the aperture transducer group in the arrangement direction is Wap, and the steering angle range in the electronic sector scanning is Ast,
the processor in the portable ultrasound probe is further configured to determine the display image region using, as the shallow image region, a region from an ultrasound transmitting and receiving surface of the transducer array to a depth Dcut represented by the following Expression (1) in the ultrasound image:

$$D\text{cut}=[(Wtr-Wap)/2]\times\tan[(180-Ast)/2] \quad (1).$$

3. The ultrasound system according to claim 1,
wherein the image information data of only the display image region determined by the processor in the portable ultrasound probe is transmitted from the portable ultrasound probe to the image display device.

4. The ultrasound system according to claim 1,
wherein the image information data is a signal obtained by performing attenuation correction according to a depth of a reflection position of the ultrasonic waves and an envelope detection process on the sound ray signal generated by the processor in the portable ultrasound probe.

5. The ultrasound system according to claim 1,
wherein the image information data is an ultrasound image signal obtained by performing attenuation correction according to a depth of a reflection position of the ultrasonic waves and an envelope detection process on the sound ray signal generated by the processor of the portable ultrasound probe and converting the sound ray signal according to a predetermined image display method.

6. The ultrasound system according to claim 1,
wherein the processor of the portable ultrasound probe is further configured to direct the transducer array to transmit the ultrasonic waves and generates the sound ray signal based on a reception signal acquired by the transducer array.

7. An ultrasound system comprising:
a portable ultrasound probe and an image display device that are connected to each other, the portable ultrasound probe performing electronic sector scanning,
wherein the portable ultrasound probe includes:
a transducer array in which a plurality of transducers are arranged in an arrangement direction; and
a processor configured to
generate a sound ray signal by directing the portable ultrasound probe to transmit and receive ultrasonic waves using an aperture transducer group consisting of ultrasound transducers which are located in a central portion in the arrangement direction among the plurality of transducers and whose number is smaller than the number of the plurality of transducers, and
generate image information data based on the sound ray signal,
the image display device includes:
a display unit configured to display an ultrasound image based on the image information data generated by the processor in the portable ultrasound probe; and
a processor configured to determine a display image region except a shallow image region including an ultrasound dead zone and having an isosceles trapezoidal shape,
the ultrasound dead zone is a region in which an intensity of an ultrasound echo in the arrangement direction is larger than the intensity of the ultrasound echo in a vertical direction perpendicular to the arrangement direction and is located in a shallow depth range and out of the steering angle in the ultrasound image, the isosceles trapezoidal shape has a lower base which has a length corresponding to the total width of the plurality of transducers in the arrangement direction, an upper base which has a length corresponding to the width of the aperture transducer group in the arrangement direction, and a height which corresponds to a depth from both ends of the transducer array in the arrangement direction to a boundary line between an inside and an outside of a steering angle range in the electronic sector scanning, and the display unit of the image display device is configured to display the ultrasound image only in the display image region determined by the processor in the image display device.

8. The ultrasound system according to claim 7,
wherein, in a case in which the width of the plurality of transducers in the arrangement direction is Wtr, the width of the aperture transducer group in the arrangement direction is Wap, and the steering angle range in the electronic sector scanning is Ast, the processor in the image display device determines the display image region using, as the shallow image region, a region from an ultrasound transmitting and receiving surface of the transducer array to a depth Dcut represented by the following Expression (1) in the ultrasound image:

$$Dcut=[(Wtr-Wap)/2]\times \tan[(180-Ast)/2] \quad (1).$$

9. The ultrasound system according to claim 7,
wherein the ultrasound image is displayed on the display unit based on the image information data of only the display image region determined by the processor in the image display device in the image information data transmitted from the portable ultrasound probe to the image display device.

10. The ultrasound system according to claim 7,
wherein the image information data is a signal obtained by performing attenuation correction according to a depth of a reflection position of the ultrasonic waves and an envelope detection process on the sound ray signal generated by the processor in the portable ultrasound probe.

11. The ultrasound system according to claim 7,
wherein the image information data is an ultrasound image signal obtained by performing attenuation correction according to a depth of a reflection position of the ultrasonic waves and an envelope detection process on the sound ray signal generated by the processor in the portable ultrasound probe and converting the sound ray signal according to a predetermined image display method.

12. The ultrasound system according to claim 7,
wherein the processor in the portable ultrasound probe directs the transducer array to transmit the ultrasonic waves and generates the sound ray signal based on a reception signal acquired by the transducer array.

13. A method for controlling an ultrasound system in which a portable ultrasound probe, which is driven by a battery and configured to perform electronic sector scanning, and an image display device are connected, the method comprising:

generating a sound ray signal by performing transmission and reception of ultrasonic waves using an aperture transducer group consisting of ultrasound transducers which are located in a central portion in an arrangement direction among a plurality of transducers arranged in a transducer array of the portable ultrasound probe and whose number is smaller than the number of the plurality of transducers;

generating image information data based on the generated sound ray signal;

transmitting the generated image information data from the portable ultrasound probe to the image display device;

determining a display image region except a shallow image region including an ultrasound dead zone and having an isosceles trapezoidal shape, the ultrasound dead zone is a region in which an intensity of an ultrasound echo in the arrangement direction is larger than the intensity of the ultrasound echo in a vertical direction perpendicular to the arrangement direction and is located in a shallow depth range and out of the steering angle in the ultrasound image, the isosceles trapezoidal shape has a lower base which has a length corresponding to the total width of the plurality of transducers in the arrangement direction, an upper base which has a length corresponding to the width of the aperture transducer group in the arrangement direction, and a height which corresponds to a depth from both ends of the transducer array in the arrangement direction to a boundary line between an inside and an outside of a steering angle range in the electronic sector scanning; and displaying the ultrasound image only in the determined display image region on a display unit of the image display device based on the image information data generated by the portable ultrasound probe.

\* \* \* \* \*